United States Patent
Whitehurst et al.

(10) Patent No.: US 7,493,172 B2
(45) Date of Patent: Feb. 17, 2009

(54) METHODS AND SYSTEMS FOR STIMULATING A NERVE ORIGINATING IN AN UPPER CERVICAL SPINE AREA TO TREAT A MEDICAL CONDITION

(75) Inventors: Todd K. Whitehurst, Santa Clarita, CA (US); Kristen N. Jaax, Saugus, CA (US); Rafael Carbunaru, Studio City, CA (US)

(73) Assignee: Boston Scientific Neuromodulation Corp., Valencia, CA (US)

( * ) Notice: Subject to any disclaimer, the term of this patent is extended or adjusted under 35 U.S.C. 154(b) by 329 days.

(21) Appl. No.: 11/073,078

(22) Filed: Mar. 4, 2005

(65) Prior Publication Data
US 2005/0154419 A1    Jul. 14, 2005

Related U.S. Application Data

(63) Continuation-in-part of application No. 10/934,155, filed on Sep. 3, 2004, which is a continuation-in-part of application No. 10/057,115, filed on Jan. 24, 2002, now Pat. No. 6,788,975.

(60) Provisional application No. 60/265,008, filed on Jan. 30, 2001, provisional application No. 60/505,831, filed on Sep. 25, 2003, provisional application No. 60/531,224, filed on Dec. 19, 2003.

(51) Int. Cl.
*A61N 1/00* (2006.01)
(52) U.S. Cl. ................. 607/117; 307/2; 307/3; 307/41
(58) Field of Classification Search ............. 607/2, 607/3, 41, 117
See application file for complete search history.

(56) References Cited

U.S. PATENT DOCUMENTS

| | | |
|---|---|---|
| 3,760,984 A | 9/1973 | Theeuwes |
| 3,845,770 A | 11/1974 | Theeuwes et al. |
| 3,916,899 A | 11/1975 | Theeuwes et al. |
| 3,923,426 A | 12/1975 | Theeuwes |
| 3,987,790 A | 10/1976 | Eckenhoff et al. |
| 3,995,631 A | 12/1976 | Higuchi et al. |
| 4,016,880 A | 4/1977 | Theeuwes et al. |
| 4,036,228 A | 7/1977 | Theeuwes |
| 4,111,202 A | 9/1978 | Theeuwes |
| 4,111,203 A | 9/1978 | Theeuwes |
| 4,203,440 A | 5/1980 | Theeuwes |
| 4,203,442 A | 5/1980 | Michaels |
| 4,210,139 A | 7/1980 | Higuchi |
| 4,327,725 A | 5/1982 | Cortese et al. |
| 4,360,019 A | 11/1982 | Portner et al. |

(Continued)

*Primary Examiner*—George Manuel
*Assistant Examiner*—Christopher A Flory
(74) *Attorney, Agent, or Firm*—AdvantEdge Law Group, LLC

(57) ABSTRACT

Methods of treating a medical condition of a patient include applying at least one stimulus to a target nerve within the patient with an implanted system control unit in accordance with one or more stimulation parameters. The target nerve may include any nerve originating in an upper cervical spine area of the patient or a branch of any nerve originating in the upper cervical spine area of the patient. Systems for treating a medical condition of a patient include a system control unit that is implanted within the patient and that is configured to apply at least one stimulus to the target nerve within the patient in accordance with one or more stimulation parameters.

20 Claims, 8 Drawing Sheets

U.S. PATENT DOCUMENTS

| | | | |
|---|---|---|---|
| 4,487,603 A | 12/1984 | Harris | |
| 4,627,850 A | 12/1986 | Deters et al. | |
| 4,692,147 A | 9/1987 | Duggan | |
| 4,702,254 A | 10/1987 | Zabara | |
| 4,725,852 A | 2/1988 | Gamblin et al. | |
| 4,865,845 A | 9/1989 | Eckenhoff et al. | |
| 4,867,164 A | 9/1989 | Zabara | |
| 5,057,318 A | 10/1991 | Magruder et al. | |
| 5,059,423 A | 10/1991 | Magruder et al. | |
| 5,112,614 A | 5/1992 | Magruder et al. | |
| 5,137,727 A | 8/1992 | Eckenhoff | |
| 5,193,539 A | 3/1993 | Schulman et al. | |
| 5,193,540 A | 3/1993 | Schulman et al. | |
| 5,215,086 A | 6/1993 | Terry, Jr. et al. | |
| 5,234,692 A | 8/1993 | Magruder et al. | |
| 5,234,693 A | 8/1993 | Magruder et al. | |
| 5,269,303 A * | 12/1993 | Wernicke et al. | 607/45 |
| 5,312,439 A | 5/1994 | Loeb | |
| 5,330,515 A * | 7/1994 | Rutecki et al. | 607/46 |
| 5,540,734 A | 7/1996 | Zabara | |
| 5,728,396 A | 3/1998 | Peery et al. | |
| 6,016,449 A * | 1/2000 | Fischell et al. | 607/45 |
| 6,051,017 A | 4/2000 | Loeb et al. | |
| 6,128,538 A * | 10/2000 | Fischell et al. | 607/45 |
| 6,161,044 A | 12/2000 | Silverstone | |
| 6,164,284 A | 12/2000 | Schulman et al. | |
| 6,185,452 B1 | 2/2001 | Schulman et al. | |
| 6,205,359 B1 | 3/2001 | Boveja | |
| 6,208,894 B1 | 3/2001 | Schulman et al. | |
| 6,356,788 B2 * | 3/2002 | Boveja | 607/45 |
| 6,360,122 B1 * | 3/2002 | Fischell et al. | 600/544 |
| 6,366,814 B1 * | 4/2002 | Boveja et al. | 607/45 |
| 6,368,315 B1 | 4/2002 | Gillis et al. | |
| 6,381,496 B1 | 4/2002 | Meadows et al. | |
| 6,405,079 B1 | 6/2002 | Ansarinia | |
| 6,427,086 B1 * | 7/2002 | Fischell et al. | 607/45 |
| 6,505,075 B1 * | 1/2003 | Weiner | 607/46 |
| 6,526,318 B1 | 2/2003 | Ansarinia | |
| 6,553,263 B1 | 4/2003 | Meadows et al. | |
| 6,647,296 B2 * | 11/2003 | Fischell et al. | 607/45 |
| 6,721,603 B2 * | 4/2004 | Zabara et al. | 607/46 |
| 6,735,475 B1 | 5/2004 | Whitehurst et al. | |
| 6,760,626 B1 | 7/2004 | Boveja | |
| 6,788,975 B1 | 9/2004 | Whitehurst et al. | |
| 2002/0198572 A1 | 12/2002 | Weiner | |
| 2003/0004549 A1 * | 1/2003 | Hill et al. | 607/9 |
| 2004/0127942 A1 * | 7/2004 | Yomtov et al. | 607/3 |
| 2004/0249429 A1 * | 12/2004 | Tadlock | 607/116 |
| 2006/0047325 A1 * | 3/2006 | Thimineur et al. | 607/45 |
| 2007/0156179 A1 * | 7/2007 | Karashurov | 607/2 |

* cited by examiner

METHODS AND SYSTEMS FOR STIMULATING A NERVE ORIGINATING IN AN UPPER CERVICAL SPINE AREA TO TREAT A MEDICAL CONDITION

RELATED APPLICATIONS

The present application is a continuation-in-part application of U.S. application Ser. No. 10/934,155, filed Sep. 3, 2004, which application is a continuation-in-part application of U.S. application Ser. No. 10/057,115, filed Jan. 24, 2002 now U.S. Pat. No. 6,788,975, issued on Sep. 7, 2004, which claims the benefit of U.S. Provisional Patent Application Ser. No. 60/265,008, filed Jan. 30, 2001. The parent application (U.S. application Ser. No. 10/934,155, filed Sep. 3, 2004) to the present application also claims the benefit of U.S. Provisional Patent Application Ser. No. 60/531,224, filed Dec. 19, 2003, and is also related to: U.S. Pat. No. 6,735,475, which patent claims the benefit of U.S. Provisional Patent Application Ser. No. 60/265,010, filed Jan. 30, 2001; and U.S. Provisional Patent Application Ser. No. 60/505,831, filed Sep. 25, 2003. All of the patents and applications mentioned above are incorporated herein by reference in their entireties.

BACKGROUND

The public health significance of many medical, psychiatric, and neurological conditions and/or disorders is often overlooked, probably because of their episodic nature and the lack of mortality attributed to them. However, some medical conditions, such as headaches and facial pain, are often incapacitating, with considerable impact on social activities and work, and may lead to significant consumption of drugs.

The International Headache Society (IHS) published "Classification and Diagnostic Criteria for Headache Disorders, Cranial Neuralgias and Facial Pain" in 1988. IHS identified 13 different general groupings of headache, given below in Table 1.

TABLE 1

Groupings of Headache Disorders and Facial Pain

1) Migraine
2) Tension-type headache
3) Cluster headache and chronic paroxysmal hemicrania
4) Miscellaneous headaches unassociated with structural lesions
5) Headache associated with head trauma
6) Headache associated with vascular disorders
7) Headache associated with non-vascular intracranial disorder
8) Headache associated with substances or their withdrawal
9) Headache associated with non-cephalic infections
10) Headaches associated with metabolic disorders
11) Headache or facial pain associated with disorder of cranium, neck, eyes, ears, nose, sinuses, teeth, mouth or other facial or cranial structures
12) Cranial neuralgias, nerve trunk pain and deafferentation pain
13) Non-classifiable headache The IHS classification of the most common types of headache is summarized in Table 2 below.

TABLE 2

IHS Classification of Primary Headaches

| | |
|---|---|
| 1. | Migraine |
| 1.1 | Migraine without aura |
| 1.2 | Migraine with aura |
| 1.2.1 | Migraine with typical aura |
| 1.2.2 | Migraine with prolonged aura |
| 1.2.3 | Familial hemiplegic migraine headache |
| 1.2.4 | Basilar migraine |
| 1.2.5 | Migraine aura without headache |
| 1.2.6 | Migraine with acute onset aura |
| 1.3 | Ophthalmoplegic migraine |
| 1.4 | Retinal migraine |
| 1.5 | Childhood periodic syndromes that may be precursors to or associated with migraine |
| 1.5.1 | Benign paroxysmal vertigo of childhood |
| 1.5.2 | Alternating hemiplegia of childhood |
| 1.6 | Complications of migraine |
| 1.6.1 | Status migrainosus |
| 1.6.2 | Migrainous infarction |
| 1.7 | Migrainous disorder not fulfilling above criteria |
| 2. | Tension-type headache |
| 2.1 | Episodic tension-type headache |
| 2.1.1 | Episodic tension-type headache associated with disorder of pericranial muscles |
| 2.1.2 | Episodic tension-type headache not associated with disorder of pericranial muscles |
| 2.2 | Chronic tension-type headache |
| 2.2.1 | Chronic tension-type headache associated with disorder of pericranial muscles |
| 2.2.2 | Chronic tension-type headache not associated with disorder of pericranial muscles |
| 2.3 | Headache of the tension-type not fulfilling above criteria |
| 3. | Cluster headache and chronic paroxysmal hemicrania |
| 3.1 | Cluster Headache |
| 3.1.1 | Cluster headache, periodicity undetermined |
| 3.1.2 | Episodic cluster headache |
| 3.1.3. | Chronic Cluster Headache |
| 3.1.3.1 | Unremitting from onset |
| 3.1.3.2 | Evolved from episodic |
| 3.2 | Chronic paroxysmal hemicrania |
| 3.3 | Cluster headache-like disorder not fulfilling above Criteria |

Migraine Headache

The IHS classification provides diagnostic criteria for migraine without and with aura, summarized in Tables 3 and 4 below.

TABLE 3

IHS Diagnostic Criteria for Migraine Without Aura

A. At least five attacks fulfilling B-D below:
B. Headache attacks lasting 4-72 hours (untreated or unsuccessfully treated)
C. Headache has at least two of the following characteristics:

1. Unilateral location
2. Pulsating quality
3. Moderate or severe intensity (inhibits or prohibits daily activities)
4. Aggravation by walking stairs or similar routine physical activity D. During headache at least one of the following:

1. Nausea and/or vomiting
2. Photophobia and phonophobia

E. At least one of the following:

1. History and physical do not suggest headaches secondary to organic or systemic metabolic disease
2. History and/or physical and/or neurologic examinations do suggest such disorder, but is ruled out by appropriate investigations
3. Such disorder is present, but migraine attacks do not occur for the first time in close temporal relation to the disorder

TABLE 4

IHS Diagnostic Criteria for Migraine With Aura

A. At least two attacks fulfilling B below:
B. At least three of the following four characteristics:

1. One or more fully reversible aura symptoms indicating focal cerebral cortical and/or brain stem dysfunction
2. At least one aura symptom develops gradually over more than four minutes or two or more symptoms occur in succession
3. No aura symptom lasts more than 60 minutes. If more than one aura symptom is present, accepted duration is proportionally increased
4. Headache follows aura with a free interval of less than 60 minutes. It may also begin before or simultaneously with the aura.

C. At least one of the following:

1. History and physical and neurologic examinations do not suggest headaches secondary to organic or systemic metabolic disease
2. History and/or physical and/or neurologic examinations do suggest such disorder, but it is ruled out by appropriate investigations
3. Such disorder is present, but migraine attacks do not occur for the first time in close temporal relation to the disorder The IHS classification includes several different types of migraine variants. Basilar migraine is defined as a migraine with an aura involving the brainstem. Symptoms include ataxia, dysarthria, vertigo, tinnitus and/or changes in consciousness and cognition. Ophthalmoplegic migraine is associated with acute attacks of third nerve palsy with accompanying dilation of the pupil. In this setting, the differential diagnosis includes an intracranial aneurysm or chronic sinusitis complicated by a mucocele. The ophthalmoplegia can last from hours to months. Hemiplegic migraine is distinguished by the accompanying hemiplegia, which can be part of the aura, or the headache may precede the onset of hemiplegia. Hemiplegic migraine can be familial and may last for days or weeks, clinically simulating a stroke. An additional differential diagnosis includes focal seizures.

Status migrainosus describes a migraine lasting longer than 72 hours with intractable debilitating pain, and typically occurs in a setting of inappropriate and prolonged use of abortive anti-migraine drugs. These patients may require hospitalization, both for pain control, detoxification from the abused drugs, and treatment of dehydration resulting from prolonged nausea and vomiting.

A migraine prevalence survey of American households was conducted in 1992, and included 20,468 respondents 12-80 years of age. Using a self-administered questionnaire based on modified IHS criteria, 17.6% of females and 5.7% of males were found to have one or more migraine headaches per year. A projection to the total US population suggests that 8.7 million females and 2.6 million males suffer from migraine headache with moderate to severe disability. Of these, 3.4 million females and 1.1 million males experience one or more attacks per month. Prevalence is highest between the ages of 25 and 55, during the peak productive years.

Based on published data, the Baltimore County Migraine Study, MEDSTAT's MarketScan medical claims data set, and statistics from the Census Bureau and the Bureau of Labor Statistics, it has been estimated that migraineurs require 3.8 bed rest days for men and 5.6 days for women each year, resulting in a total of 112 million bedridden days. Migraine costs American employers about $13 billion a year because of missed workdays and impaired work function—close to $8 billion is directly due to missed workdays. Patients of both sexes aged 30 to 49 years incurred higher indirect costs compared with younger or older employed patients. Annual direct medical costs for migraine care are about $1 billion, with about $100 spent per diagnosed patient. Physician office visits account for about 60% of all costs; in contrast, emergency department visits contribute less than 1% of the direct costs.

Tension-Type Headache

The diagnostic criteria for tension-type headaches are summarized in Table 5 below. However, migraine symptoms may overlap considerably with those of tension-type headaches. Tension-type headaches are believed by some experts to be a mild variant of migraine headache. Patients with tension-type headaches who also have migraines may experience nausea and vomiting with a tension headache, though when they do, it typically is mild and for a shorter duration compared to that with a migraine. Tension-type headache may be a disorder unto itself in individuals who do not have migraines, and may manifest as attacks of mild migraine in individuals with migraines.

TABLE 5

IHS Criteria for Various Forms of Tension-Type Headache

Tension-type headache

At least two of the following pain characteristics:

1. Pressing/tightening (non-pulsating) quality
2. Mild or moderate intensity (may inhibit, but does not prohibit activities)
3. Bilateral location
4. No aggravation by walking stairs or similar routine physical activity Both of the following:

1. No nausea or vomiting (anorexia may occur)
2. Photophobia and phonophobia absent, or only one is present At least one of the following:

1. History and physical do not suggest headaches secondary to organic or systemic metabolic disease
2. History and/or physical and/or neurologic examinations do suggest such disorder, but is ruled out by appropriate investigations
3. Such disorder is present, but tension-type headache does not occur for the first time in close temporal relation to the disorder Episodic tension-type headache (ETTH)

Diagnostic criteria:

A. At least 10 previous episodes, <180 days/year (<15/mo) with headache
B. Headache lasting from 30 minutes to 7 days Chronic tension-type headache (CTTH)

Diagnostic criteria:

A. Average frequency ≧1 day/month (≧189 days/year) for ≧6 months

Tension-type headache associated with disorder of pericranial muscles

At least one of the following:

1. Increased tenderness of pericranial muscles demonstrated by manual palpation or pressure algometer.
2. Increased electromyographic level of pericranial muscles at rest or during physiologic tests.

Tension-type headache not associated with pericranial muscle disorder

No increased tenderness of pericranial muscles. If studied, electromyography of pericranial muscles shows normal levels of activity.

Based on a telephone survey of 13,345 people, the 1-year period prevalence of episodic tension-type headache (ETTH) is estimated to be 38.3%, according to IHS criteria. Women had a higher 1-year ETTH prevalence than men in all age, race, and education groups, with an overall prevalence ratio of 1.16. Prevalence peaked in the 30- to 39-year-old age group in both men (42.3%) and women (46.9%). Prevalence increased with increasing educational levels in both sexes, reaching a peak in subjects with graduate school educations of 48.5% for men and 48.9% for women. Of subjects with ETTH, 8.3% reported lost workdays because of their headaches, while 43.6% reported decreased effectiveness at work, home, or school.

Chronic Daily Headache

Chronic tension-type headache (CTTH) is a subtype of tension headaches, with patients experiencing headaches daily or almost every day. In practice, the term "chronic daily headache" is commonly used to describe headaches lasting for greater than 4 hours per day and for at least 15 days per month. The classification of chronic daily headaches is summarized below in Table 6.

TABLE 6

Classification of Chronic Daily Headache

Transformed migraine

1. With medication overuse
2. Without medication overuse

Chronic tension-type headache (CTTH)

1. With medication overuse
2. Without medication overuse

New daily persistent headache

1. With medication overuse
2. Without medication overuse

Hemicrania continua

1. With medication overuse
2. Without medication overuse

In the study of 13,345 people cited above, the 1-year period prevalence of chronic tension-type headache (CTTH) was estimated to be 2.2%. This prevalence was higher in women and declined with increasing education. Subjects with CTTH reported more lost workdays (mean of 27.4 days vs. 8.9 days for those reporting lost workdays) and reduced-effectiveness days (mean of 20.4 vs. 5.0 days for those reporting reduced effectiveness) compared with subjects with ETTH.

Chronic daily headaches are best conceptualized as an umbrella category term referring to a group of headache disorders characterized by headaches which occur greater than 15 days per month, with an average untreated duration of greater than 4 hours per day. There are many secondary causes of chronic daily headache, including post-traumatic headache, arthritis, intracranial mass lesions, etc. There are also short-lived primary headache disorders that occur greater than 15 days per month, such as chronic cluster headache or the paroxysmal hemicranias. The most common primary, chronic daily headache disorders include transformed migraine, chronic tension-type headaches, new daily persistent headache, or hemicrania continua. Each of these diagnoses can be complicated by medication overuse (e.g., barbiturates, acetaminophen, aspirin, caffeine, ergotamine tartrate and opioids). When used daily, all of these medications can lead to a vicious cycle of rebound headaches.

Cluster Headache

The 1988 IHS classification system recognized the uniqueness of cluster headache as a clinical and epidemiological entity. Formerly classified as a vascular migraine variant, cluster headache (a.k.a. suicide headache) is thought to be one of the most severe headache syndromes. It is characterized by attacks of severe pain, generally unilateral and orbital and lasting 15 minutes to 3 hours, with one or more symptoms such as unilateral rhinorrhea, nasal congestion, lacrimation, and conjunctival injection. In most patients, headaches occur in episodes, generally with a regular time pattern. These "cluster periods" last for weeks to months, separated by periods of remission lasting months to years. These headaches primarily affect men and in many cases patients having distinguishing facial, body, and psychological features. Several factors may precipitate cluster headaches, including histamine, nitroglycerin, alcohol, transition from rapid eye movement (REM) to non-REM sleep, circadian periodicity, environmental alterations, and change in the level of physical, emotional, or mental activity. The IHS classification system gives specific diagnostic criteria for cluster headache, as given in Table 7 below.

TABLE 7

IHS Diagnostic Criteria for Cluster Headache 3.1 Cluster Headache

A. At least 5 attacks fulfilling B-D below:
B. Severe unilateral, orbital, supraorbital and/or temporal pain lasting 15-180 minutes untreated
C. At least one of the following signs present on the pain side:
  1.  Conjunctival injection
  2.  Lacrimation
  3.  Nasal congestion
  4.  Rhinorrhea
  5.  Forehead and facial sweating
  6.  Miosis
  7.  Ptosis
  8.  Eyelid edema
D. Frequency of attacks: from 1 every other day to 8 per day
E. At least one of the following:
  1.  History, physical and neurological examinations do not suggest one of the disorders listed in groups 5-11 of Table 1
  2.  History and/or physical and/or neurological examinations do suggest such disorder, but it is ruled out by appropriate investigations
  3.  Such disorder is present, but cluster headache does not occur for the first time in close temporal relation to the disorder 3.1.1 Cluster headache periodicity undefined A. Criteria for 3.1 fulfilled
B. Too early to classify as 3.1.2 or 3.1.3

3.1.2 Episodic cluster headache

Description: Attacks lasting between 1 week and 3 months occur in periods lasting 1 week to one year separated by pain free periods lasting 14 days or more.
A. All the letter headings of 3.1
B. At least 2 periods of headaches (cluster periods lasting (untreated) from 7 days to one year, separated by remissions of at least 14 days.

3.1.3 Chronic cluster headache

Description: Attacks lasting between 2 weeks and 3 months occur for more than one year without remission or with remissions lasting less than 14 days.
A. All the letter headings of 3.1
B. Absence of remission phases for one year or more or with remissions lasting less than 14 days.

3.1.3.1 Chronic cluster headache unremitting from onset

A. All the letter headings of 3.1.3
B. Absence of remission periods lasting 14 days or more from onset.

3.1.3.2 Chronic cluster headache evolved from episodic

A. All the letter headings of 3.1.3
B. At least one interim remission period lasting 14 days or more within one year after onset, followed by unremitting course for at least one year.

The estimated prevalence of cluster headache is 69 cases per 100,000 people. Men are affected more commonly than women in a proportion of 6:1. Although most patients begin experiencing headache between the ages of 20 and 50 years (mean of 30 years), the syndrome may begin as early as the first decade and as late as the eighth decade.

Cervicogenic Headache

Cervicogenic headache (CEH) is a headache with its origin in the neck area. The source of pain is in structures around the neck that have been damaged. These structures can include joints, ligaments, muscles, and cervical discs, all of which have complex nerve endings. When these structures are damaged, the nerve endings send pain signals up the pathway from the upper nerves of the neck to the brainstem. These nerve fibers may synapse in the same brainstem nuclei as the nerve fibers of the trigeminal nerve. Since the trigeminal nerve is responsible for the perception of head pain, the patient experiences the symptoms of headache and/or facial pain.

While many patients who are diagnosed with CEH have the traditional symptoms of tension-type headache, some of the patients who have the traditional symptoms of migraine and cluster headache also respond to CEH diagnosis and treatment.

Facial Pain

Facial pain may be due to a number of underlying disorders. Among the most common is Trigeminal Neuralgia (also known as tic douloureux). More than 50,000 people in the United States suffer from trigeminal neuralgia. This disorder may cause episodes of intense, stabbing, electric shock-like pain in the areas of the face where the branches of the nerve are distributed (e.g., the lips, eyes, nose, scalp, forehead, upper jaw, and lower jaw). A less common form of the disorder, Atypical Trigeminal Neuralgia, may cause less intense, constant, dull burning or aching pain, sometimes with occasional electric shock-like stabs. Both forms of the disorder most often affect one side of the face, but some patients experience pain at different times on both sides. Onset of symptoms occurs most often after age 50, and it affects women more often than men. For patients with this disorder, an ordinary touch of the face, such as when brushing teeth or applying makeup, can trigger an attack. Trigeminal neuralgia is believed to be due to hyper-excitability of fibers of the trigeminal nerve or its ganglion. Microelectrode recordings from the trigeminal ganglion have demonstrated sustained high-frequency bursts during pain episodes of trigeminal neuralgia.

Trigeminal neuralgia may be treated medically with drugs that decrease neural excitability, e.g., carbamazepine or phenytoin. However, such medications prove ineffective for many patients over the course of the disease. Thus, a number of surgical interventions (e.g., microvascular decompression of the trigeminal ganglion or it nerve fibers, radio-frequency rhizotomy) have been developed.

Another cause of facial pain is Temporomandibular Joint (TMJ) Dysfunction Syndrome. Most TMJ discomfort is temporary and can be treated with inexpensive remedies. However, some TMJ dysfunction patients are afflicted with persistent and sometimes unbearable pain. The symptoms of this chronic dysfunction include persistent pain in the facial muscles on one or both sides, a clicking or popping sensation when opening the mouth or working the jaw, recurring headaches, and difficulty chewing. Analgesics and anti-inflammatory medication may relieve the pain in some patients. Others turn to TMJ surgery in desperation.

Yet another cause of facial pain is Postherpetic Neuralgia, which is a possible complication of herpes zoster reactivation ("shingles"). The herpes zoster virus may cause chicken pox upon initial infection. When reactivated, the virus causes shingles—a painful disease characterized by eruptions along a nerve path often accompanied by severe neuralgia and a skin rash. It can affect the torso or limbs (spinal ganglia shingles) or the face (trigeminal ganglia shingles). Approximately one in five adults develops shingles, usually after age 50. For most people, shingles is an acute condition with pain typically lasting one month. However, in older patients or patients with a compromised immune system, singles can lead to postherpetic neuralgia, a very painful chronic condition in which the pain associated with the shingles persists beyond one month, even after the rash is gone. The incidence of postherpetic neuralgia is almost negligible before age 50, but at least 50% of patients older than 60 years and almost 75% beyond age 70 become affected following a shingles attack. Postherpetic neuralgia tends to improve over time without treatment. Some estimates suggest that only two to three percent of patients have pain lasting more than one year. However, since more than 60,000 new cases develop annually in the US, the collective morbidity is still substantial. Treatment of postherpetic neuralgia consists of symptomatic relief of severe pain with tricyclic antidepressants and opioids.

Epilepsy

Epilepsy is characterized by a tendency to recurrent seizures that can lead to loss of awareness, loss of consciousness, and/or disturbances of movement, autonomic function, sensation (including vision, hearing and taste), mood, and/or mental function. Epilepsy afflicts one to two percent of the population in the developed world. The mean prevalence of active epilepsy (i.e., continuing seizures or the need for treatment) in developed and undeveloped countries combined is estimated to be 7 per 1,000 of the general population, or approximately 40 million people worldwide. Studies in developed countries suggest an annual incidence of epilepsy of approximately 50 per 100,000 of the general population. However, studies in developing countries suggest this figure is nearly double at 100 per 100,000.

Epilepsy is often but not always the result of an underlying brain disease. Any type of brain disease can cause epilepsy, but not all patients with the same brain pathology will develop epilepsy. The cause of epilepsy cannot be determined in a number of patients; however, the most commonly accepted theory posits that it is the result of an imbalance of certain chemicals in the brain, e.g., neurotransmitters. Children and adolescents are more likely to have epilepsy of unknown or genetic origin. The older the patient, the more likely it is that the cause is an underlying brain disease such as a brain tumor or cerebrovascular disease.

Trauma and brain infection can cause epilepsy at any age, and in particular, account for the higher incidence rate in developing countries. For example, in Latin America, neurocysticercosis (cysts on the brain caused by tapeworm infection) is a common cause of epilepsy. In Africa, AIDS and its related infections, malaria and meningitis, are common causes. In India, AIDS, neurocysticercosis and tuberculosis, are common causes. Febrile illness of any kind, whether or not it involves the brain, can trigger seizures in vulnerable young children, which seizures are called febrile convulsions. About 5% of such children go on to develop epilepsy later in life. Furthermore, for any brain disease, only a proportion of sufferers will experience seizures as a symptom of that disease. It is therefore suspected that those who do experience such symptomatic seizures are more vulnerable for similar biochemical/neurotransmitter reasons.

SUMMARY

Methods of treating a medical condition of a patient include applying at least one stimulus to a target nerve within the patient with an implanted system control unit in accordance with one or more stimulation parameters. The target nerve may include any nerve originating in an upper cervical spine area of the patient or a branch of any nerve originating in the upper cervical spine area of the patient.

Systems for treating a medical condition of a patient include a system control unit that is implanted within the patient and that is configured to apply at least one stimulus to a target nerve within the patient in accordance with one or more stimulation parameters. The target nerve may include any nerve originating in an upper cervical spine area of the patient or a branch of any nerve originating in the upper cervical spine area of the patient.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical, elements.

DETAILED DESCRIPTION

Figure 1A:
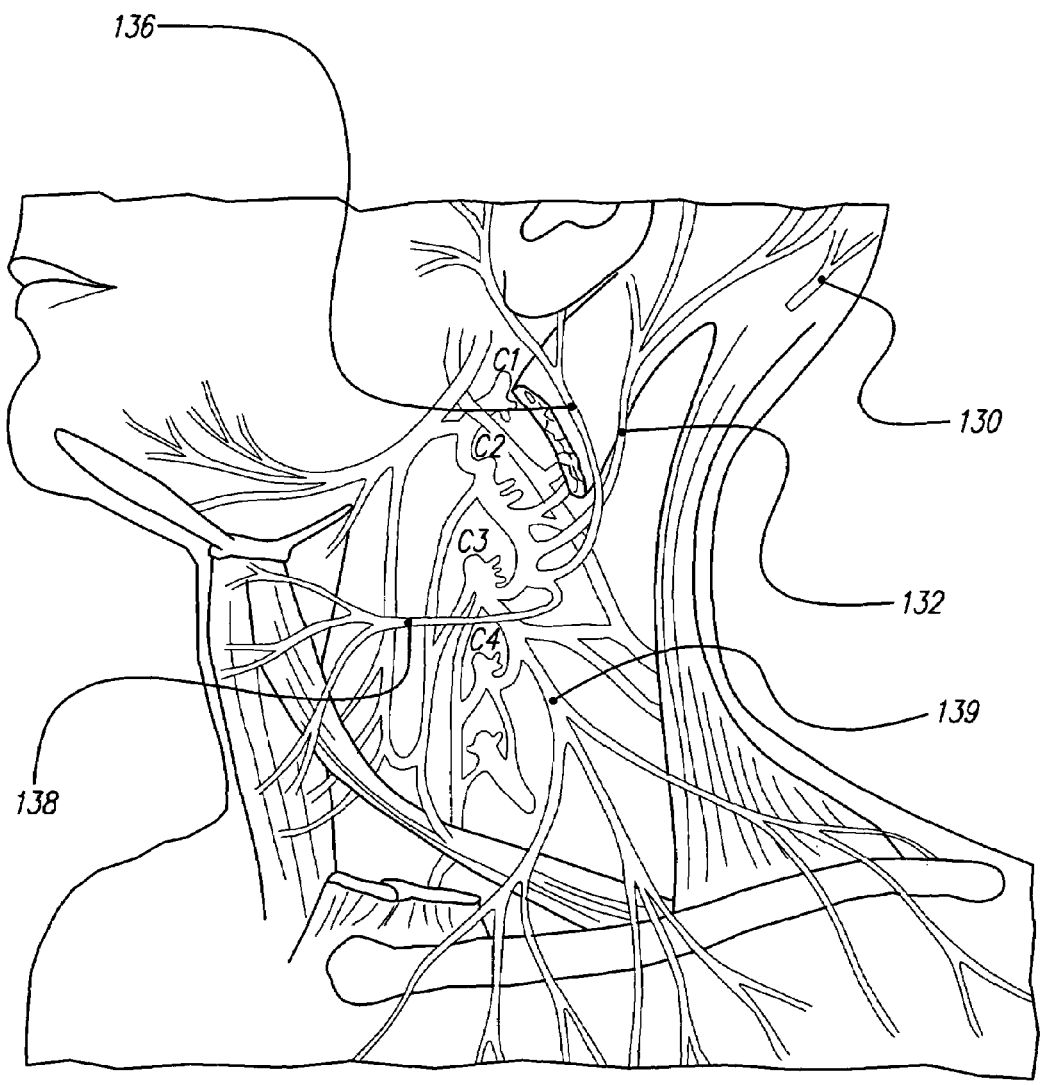
FIG. 1A depicts the upper cervical spine area of a patient and shows a number of nerves originating in the upper cervical spine area according to principles described herein.

Methods and systems for treating many different types of medical, psychiatric, and neurological conditions and/or disorders of varying degrees are described herein. A system control unit (SCU) is implanted within a patient. The SCU may include, for example, a microstimulator stimulates a target nerve. In some cases, the microstimulator is coupled directly to the target nerve. In some alternative embodiments, the SCU may include an implantable pulse generator (IPG) coupled to a number of electrodes that are coupled to the target nerve. The SCU is configured to apply at least one stimulus to one or more nerves originating in an upper cervical spine area of the patient in accordance with one or more stimulation parameters. The stimulus is configured to treat one or more medical, psychiatric, and/or neurological conditions and/or disorders and may include electrical stimulation, drug stimulation, or both. Consequently, as used herein and in the appended claims, the term "stimulus" or "stimulation," unless otherwise indicated, will broadly refer to either an electrical stimulation, a drug stimulation, or both.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

As will be described in more detail below, there exist many different types of medical, psychiatric, and neurological conditions and/or disorders of varying degrees for which researchers have found potential causes. However, the exact causes of many medical, psychiatric, and neurological conditions and disorders remain unknown. Consequently, many techniques have been presented to treat these conditions and disorders. These techniques have had varying levels of success. Potential causes and treatments for some medical conditions will be discussed below, including headaches, facial pain, and epilepsy. However, it will be recognized that headaches, facial pain, and epilepsy are merely illustrative of the many different types of medical, psychiatric, and neurological conditions and disorders that exist and may be treated according to the principles described herein.

Headache and Facial Pain

The mechanism of a migraine is not well understood. Prevalent theories suggest that a migraine is a central nervous system neurovascular disorder and that the trigeminal nerve may play a prominent role. The trigeminal nerve carries virtually all of the sensation from the face, and thus it likely plays a role in any pain felt at the front or the top of the head.

In "Pathophysiology of migraine—new insights" (*Canadian Journal of Neurological Sciences*, November 1999), Hargreaves, et al. state that "the exact nature of the central dysfunction that is produced in migraines is still not clear and may involve spreading depression-like phenomena and activation of brainstem monoaminergic nuclei that are part of the central autonomic, vascular, and pain control centers. It is generally thought that local vasodilation of intracranial extracerebral blood vessels and a consequent stimulation of surrounding trigeminal sensory nervous pain pathways is a key mechanism underlying the generation of headache pain associated with migraine. This activation of the trigeminovascular system is thought to cause the release of vasoactive sensory neuropeptides, especially CGRP, that increase the pain response. The activated trigeminal nerves convey nociceptive information to central neurons in the brain stem trigeminal sensory nuclei that in turn relay the pain signals to higher centers where headache pain is perceived. It has been hypothesized that these central neurons may become sensitized as a migraine attack progresses." The disorder of migraine may ultimately evoke changes in blood vessels within pain-producing intracranial meningeal structures that give rise to headache pain.

Hargreaves, et al. further state that "the 'triptan' anti-migraine agents (e.g., sumatriptan, rizatriptan, zolmitriptan, and naratriptan) are serotonergic agonists that have been shown to act selectively by causing vasoconstriction through 5 HT1B receptors that are expressed in human intracranial arteries and by inhibiting nociceptive transmission through an action at 5-HT1D receptors on peripheral trigeminal sensory nerve terminals in the meninges and central terminals in brainstem sensory nuclei. These three complementary sites of action underlie the clinical effectiveness of the 5 HT1B/1D agonists against migraine headache pain and its associated symptoms."

In "Current concepts of migraine pathophysiology" (*Canadian Journal of Neurological Sciences*, Autumn 1999), Hamel cites evidence that indicates migraine originates in the brain and, in its process and evolution, affects the meningeal blood vessels and leads to the development of head pain. Hamel states that "this manifestation is related to the activation of the trigeminovascular sensory nerves, which release neuropeptides that mediate vasodilation, and the proinflammatory reaction thought to be involved in pain generation and transmission. Such a concept underscores the fact that the relationship between the nerves and the blood vessels is of paramount importance in the manifestation of the disease's symptoms."

It has also been suggested that primary headache syndromes, such as cluster headache and migraine, share an anatomical and physiologic substrate, namely the neural innervation of the cranial circulation. In "The Trigeminovascular System in Humans: Pathophysiologic Implications for Primary Headache Syndromes of the Neural Influences on the Cerebral Circulation" (*Journal of Cerebral Blood Flow Metabolism*, February 1999), May, et al. report that observations of vasodilation were made in an experimental trigeminal pain study. They conclude that the observed dilation of these vessels in trigeminal pain is not inherent to a specific headache syndrome, but rather is a feature of the trigeminal neural innervation of the cranial circulation. They also state that clinical and animal data suggest that the observed vasodilation is, in part, an effect of a trigeminoparasympathetic reflex. They suggest that the trigeminal innervation of the cranial circulation and the observed vasodilation of the associated vasculature during headache syndromes may be an underlying pathophysiological mechanism of headache.

In "Intraoral Chilling versus Oral Sumatriptan for Acute Migraine" (*Heart Disease*, November-December 2001), Friedman, et al. state that "recent evidence suggests that the primary inflammation occurs in the maxillary nerve segment [of the trigeminal nerve], accessible intraorally. Local tenderness, related to symptom laterality, has been palpated in asymptomatic migraine patients."

In "Cluster Headache" (*Current Treatment Options in Neurology*, November 1999), Salvesen suggests a possible link between the trigeminal nerve and cluster headache: "for a very limited group of patients with chronic cluster headache, surgery may be a last resort. The best surgical options are probably radio-frequency rhizotomy or microvascular decompression of the trigeminal nerve."

In a recent study involving eighteen patients, fifteen patients obtained immediate pain relief from chronic intractable cluster headaches after one or two injections of percutaneous retrogasserian glycerol rhizolysis. However, cluster headache recurred in seven patients over the course of the study, suggesting that permanent trigeminal destruction may not be an effective treatment.

For many years, Transcutaneous Electrical Nerve Stimulation (TENS) has been applied with some success to the control of headache and facial pain symptoms. TENS is used to modulate the stimulus transmissions by which pain is felt by applying low-voltage electrical stimulation to large peripheral nerve fibers via electrodes placed on the skin. A study of 282 migraineurs had patients undergo Punctual (i.e., episodic) Transcutaneous Electrical Nerve Stimulation (PuTENS) via pocket electrostimulators. After more than 6 months PuTENS was prophylactically effective in eighty percent of the patients in the study, i.e., their frequency of attacks and use of drugs were reduced by at least fifty percent. However, TENS devices can produce significant discomfort and can only be used intermittently.

Epilepsy

Recent studies in both developed and developing countries have shown that up to 70 percent of newly diagnosed children and adults with epilepsy can be successfully treated (i.e., complete control of seizures for several years) with antiepileptic drugs. After two to five years of successful treatment, drugs can be withdrawn in about 70 percent of children and 60 percent of adults without the patient experiencing relapses. However, up to 30 percent of patients are refractory to medication. There is evidence that the longer the history of epilepsy, the harder it is to control. The presence of an underlying brain disease typically results in a worse prognosis in terms of seizure control. Additionally, partial seizures, especially if associated with brain disease, are more difficult to control than generalized seizures.

Patients suffering from epilepsy may undergo surgery to remove a part of the brain in which the seizures are believed to arise, i.e., the seizure focus. However, in many patients a seizure focus cannot be identified, and in others the focus is in an area that cannot be removed without significant detrimental impact on the patient. For example, in temporal lobe epilepsy, patients may have a seizure focus in the hippocampi bilaterally. However, both hippocampi cannot be removed without adversely affecting a patient's long-term memory. Other patients may have a seizure focus that lies adjacent to a critical area such as the speech center.

Vagus nerve stimulation (VNS) has been applied with partial success in patients with refractory epilepsy. In this procedure, an implantable pulse generator (IPG) is implanted in the patient's thorax, and an electrode lead is routed from the IPG to the left vagus nerve in the neck. Based on a number of studies, approximately five percent of patients undergoing VNS are seizure-free, and an additional 30-40 percent of patients have a greater than 50 percent reduction in seizure frequency.

In addition to this relatively low efficacy, VNS may lead to significant side effects. The vagus nerve provides parasympathetic innervation to the cardiac tissue, and thus VNS may lead to bradycardia, arrhythmia, or even graver cardiac side effects. In fact, VNS systems may only be used on the left vagus nerve, as the right vagus nerve contributes significantly more to cardiac innervation. Additionally, VNS may interfere with proper opening of the vocal cords, which has led to hoarseness and shortness of breath in a significant number of VNS patients.

The exact mechanism of seizure suppression using VNS is unknown. The nucleus of tractus solitarius (NTS; a.k.a., nucleus of the solitary tract) is a primary site at which vagal afferents terminate. Because afferent vagal nerve stimulation has been demonstrated to have anticonvulsant effects, it is likely that changes in synaptic transmission in the NTS can regulate seizure susceptibility. To demonstrate this, Walker, et al. ("Regulation of limbic motor seizures by GABA and glutamate transmission in nucleus tractus solitarius," *Epilepsia*, August 1999) applied muscimol, an agonist of the inhibitory neurotransmitter GABA, to the NTS in a murine model of epilepsy. Muscimol applied to the NTS attenuated seizures in all seizure models tested, whereas muscimol applied to adjacent regions of NTS had no effect. Additionally, bicuculline methiodide, a GABA antagonist, injected into the NTS did not alter seizure responses. Finally, anticonvulsant effects were also obtained with application of lidocaine, a local anesthetic, into the NTS. Unilateral injections were sufficient to afford seizure protection. Walker, et al. conclude that inhibition of the NTS outputs enhances seizure resistance in the forebrain and provides a potential mechanism for the seizure protection obtained with vagal stimulation.

The NTS sends fibers bilaterally to the reticular formation and hypothalamus, which are important in the reflex control of cardiovascular, respiratory, and gastrointestinal functions. The NTS also provides input to the dorsal motor nucleus of the vagus, which enables the parasympathetic fibers of the vagus nerve to control these reflex responses. The NTS runs the entire length of the medulla oblongata, and the NTS (as well as the trigeminal nuclei) receives somatic sensory input from all cranial nerves, with much of its input coming from the vagus nerve.

Convincing evidence has been given that a significant number of neurons in the trigeminal nerve project to the NTS. By applying horseradish peroxidase to peripheral branches of the trigeminal nerve in a cat, it was found that branches of the trigeminal nerve (the lingual and pterygopalatine nerves) were found to contain fibers which ended ipsilaterally in the rostral portions of the NTS, massively in the medial and ventrolateral NTS, moderately in the intermediate and interstitial NTS, and sparsely in the ventral NTS. (The rostralmost part of the NTS was free from labeled terminals.) After injecting the enzyme into the NTS portions rostral to the area postrema, small neurons were scattered in the maxillary and mandibular divisions of the trigeminal ganglion. It was concluded that trigeminal primary afferent neurons project directly to the NTS. By staining for substance P immunoreactivity, it was found that Substance P containing trigeminal sensory neurons project to the NTS.

Convincing evidence has also been reported that a significant number of neurons in the trigeminal nuclei project to the NTS. Menetrey, et al used the retrograde transport of a protein-gold complex to examine the distribution of spinal cord and trigeminal nucleus caudalis neurons that project to the NTS in the rat. [See Menetrey, et al. "Spinal and trigeminal projections to the nucleus of the solitary tract: a possible substrate for somatovisceral and viscerovisceral reflex activation." *J Comp Neurol* 1987 Jan. 15;255(3):439-50.] The authors found that retrogradely labeled cells were numerous in the superficial laminae of the trigeminal nucleus caudalis, through its rostrocaudal extent. Since the NTS is an important relay for visceral afferents from both the glossopharyngeal and vagus nerves, the authors suggest that the spinal and trigeminal neurons that project to the NTS may be part of a larger system that integrates somatic and visceral afferent inputs from wide areas of the body. The projections may underlie somatovisceral and/or viscerovisceral reflexes, perhaps with a significant afferent nociceptive component.

Another study utilized microinfusion and retrograde transport of D [3H] aspartate to identify excitatory afferents to the NTS. The authors found that the heaviest labeling was localized bilaterally in the trigeminal nucleus with cells extending through its subdivisions and the entire rostrocaudal axis.

In addition, a study by Fanselow, et al. ("Reduction of pentylenetetrazole-induced seizure activity in awake rats by seizure-triggered trigeminal nerve stimulation," *Journal of Neuroscience*, November 2000) demonstrated that unilateral stimulation via a chronically implanted nerve cuff electrode applied to the infraorbital branch of the trigeminal nerve led to a reduction in electrographic seizure activity of up to 78 percent. The authors reported that bilateral trigeminal stimulation was even more effective.

The thalamus is believed to play a major role in some types of epilepsy by acting as a center for seizure onset or as a relay station in allowing a focal seizure to propagate. In a Single Positron Emission Computed Tomography (SPECT) study of patients with left-sided VNS systems, a consistent decrease of activity was found in the left thalamus caused by VNS. The authors concluded that left-sided VNS reduces seizure onset or propagation through inhibition of the thalamic relay center.

Thalamic relay neurons are essential in generating 3 Hz absence seizures and are believed to be involved in other types of epilepsy. Thalamic nuclei of some patients suffering from epilepsy display neuronal activities described as "low-threshold calcium spike bursts," which have been shown to be related to a state of membrane hyperpolarization of thalamic relay neurons. This thalamic rhythmicity is transmitted to the related cortex, thanks to thalamocortical resonant properties. In the cortex, an asymmetrical corticocortical inhibition (edge effect) at the junction between low and high frequency zones is proposed to be at the origin of a cortical activation of high frequency areas bordering low frequency ones.

Other Medical, Psychiatric, and Neurological Conditions and Disorders

Other medical, psychiatric, and neurological conditions and/or disorders include, but are not limited to, the following:

1) Pain resulting from one or more medical conditions including, but not limited to: migraine headaches, including but not limited to migraine headaches with aura, migraine headaches without aura, menstrual migraines, migraine variants, atypical migraines, complicated migraines, hemiplegic migraines, transformed migraines, and chronic daily migraines; episodic tension headaches; chronic tension headaches; analgesic rebound headaches; episodic cluster headaches; chronic cluster headaches; cluster variants; chronic paroxysmal hemicrania; hemicrania continua; post-traumatic headache; post-traumatic neck pain; post-herpetic neuralgia involving the head or face; pain from spine fracture secondary to osteoporosis; arthritis pain in the spine, headache related to cerebrovascular disease and stroke; headache due to vascular disorder; musculoskeletal neck pain; reflex sympathetic dystrophy, cervicalgia; glossodynia, carotidynia; cricoidynia; otalgia due to middle ear lesion; gastric pain; sciatica; maxillary neuralgia; laryngeal pain, myalgia of neck muscles; trigeminal neuralgia; post-lumbar puncture headache; low cerebro-spinal fluid pressure headache; temporomandibular joint disorder; atypical facial pain; ciliary neuralgia; paratrigeminal neuralgia; petrosal neuralgia; Eagle's syndrome; idiopathic intracranial hypertension; orofacial pain; myofascial pain syndrome involving the head, neck, and shoulder; chronic migraneous neuralgia, cervical headache; paratrigeminal paralysis; sphenopalatine ganglion neuralgia; carotidynia; Vidian neuralgia; and causalgia.

2) Epilepsy, including, but not limited to, generalized and partial seizure disorders.

3) Cerebrovascular diseases resulting from one or more medical conditions including, but not limited to, atherosclerosis, aneurysms, strokes, and cerebral hemorrhage.

4) Autoimmune diseases resulting from one or more medical conditions including, but not limited to, multiple sclerosis.

5) Sleep disorders resulting from one or more medical conditions including, but not limited to, sleep apnea and parasomnias.

6) Autonomic disorders resulting from one or more medical conditions including, but not limited to: gastrointestinal disorders, including, but not limited to, gastrointestinal motility disorders, nausea, vomiting, diarrhea, chronic hiccups, gastroesphageal reflux disease, and hypersecretion of gastric acid; autonomic insufficiency; excessive epiphoresis; excessive rhinorrhea; and cardiovascular disorders including, but not limited to, cardiac dysrythmias and arrythmias, hypertension, and carotid sinus disease.

7) Urinary bladder disorders resulting from one or more medical conditions including, but not limited to, spastic and flaccid bladder.

8) Abnormal metabolic states resulting from one or more medical conditions including, but not limited to, hyperthyroidism and hypothyroidism.

9) Disorders of the muscular system resulting from one or more medical conditions including, but not limited to, muscular dystrophy and spasms of the upper respiratory tract and face.

10) Neuropsychiatric disorders resulting from one or more medical conditions including, but not limited to, depression, schizophrenia, bipolar disorder, autism, personality disorders, and obsessive-compulsive disorder.

For ease of explanation, the term "medical condition" will be used herein and in the appended claims, unless otherwise specifically denoted, to refer to any medical, psychiatric, and/or neurological condition and/or disorder described herein, listed above, or related or similar to any condition or disorder described or listed herein.

Figure 1B:
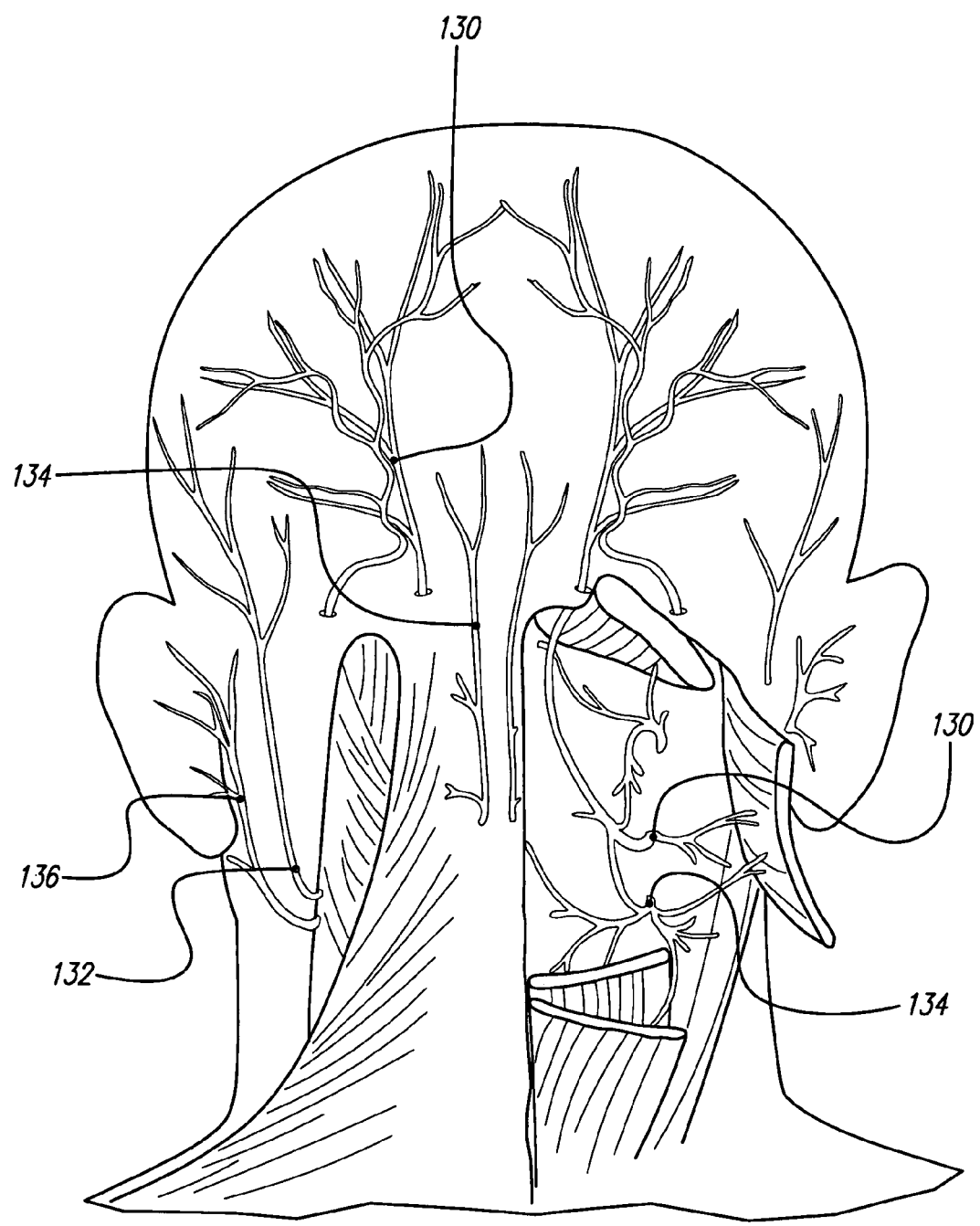
FIG. 1B shows various nerves in the back of the head and neck according to principles described herein.

FIGS. 1A and 1B depict the upper cervical spine (C1-C4) area of a patient. As shown in FIGS. 1A and 1B, a number of nerves arise from the upper cervical spine (C1-C4). Examples of such nerves include, but are not limited to, the greater occipital nerve(s) (130), the lesser occipital nerve(s) (132), the third occipital nerve(s) (134), greater auricular nerve(s) (136), transverse cervical nerve(s) (138), the supraclavicular nerve(s) (139), and/or branches of any of these nerves. As shown in FIG. 1B, the occipital nerves (130, 132, 134) are relatively easily accessed, especially in their distal portions, since they lie subcutaneously in the back of the head and upper neck.

In some embodiments, at least one stimulus is applied with a system control unit (SCU) to one or more target nerves of a patient to treat and/or prevent one or more of the medical conditions listed above. As used herein and in the appended claims, the term "target nerve" will refer to any nerve originating in the upper cervical spine area (i.e., C1-C4) or any branch of a nerve originating in the upper cervical spine area. For example, the target nerve may include, but is not limited to, the greater occipital nerve(s) (130), the lesser occipital nerve(s) (132), the third occipital nerve(s) (134), greater auricular nerve(s) (136), transverse cervical nerve(s) (138), the supraclavicular nerve(s) (139), and/or branches of any of these nerves. The greater (130), lesser (132), and third occipital nerves (134), as well as the greater auricular nerves (136), are relatively easily accessed, especially in their distal portions, since they lie subcutaneously in the back of the head and upper neck. An SCU may thus be easily implanted via injection and/or via endoscopic means adjacent to one or more of these nerves. A more complicated surgical procedure may be required for sufficient access to one or more of these nerves and/or for purposes of fixing the SCU in place. The sites of injection or skin incision may be selected such that the resulting scars would likely be covered by hair on most people.

The stimulus applied to the target nerve may include electrical stimulation, also known as neuromodulation. Electrical stimulation will be described in more detail below. The stimulus may additionally or alternatively include drug stimulation. As will be described in more detail below, therapeutic dosages of one or more drugs may be infused into a target nerve or into a site near the target nerve to treat any of the above-mentioned medical conditions.

Figure 2:
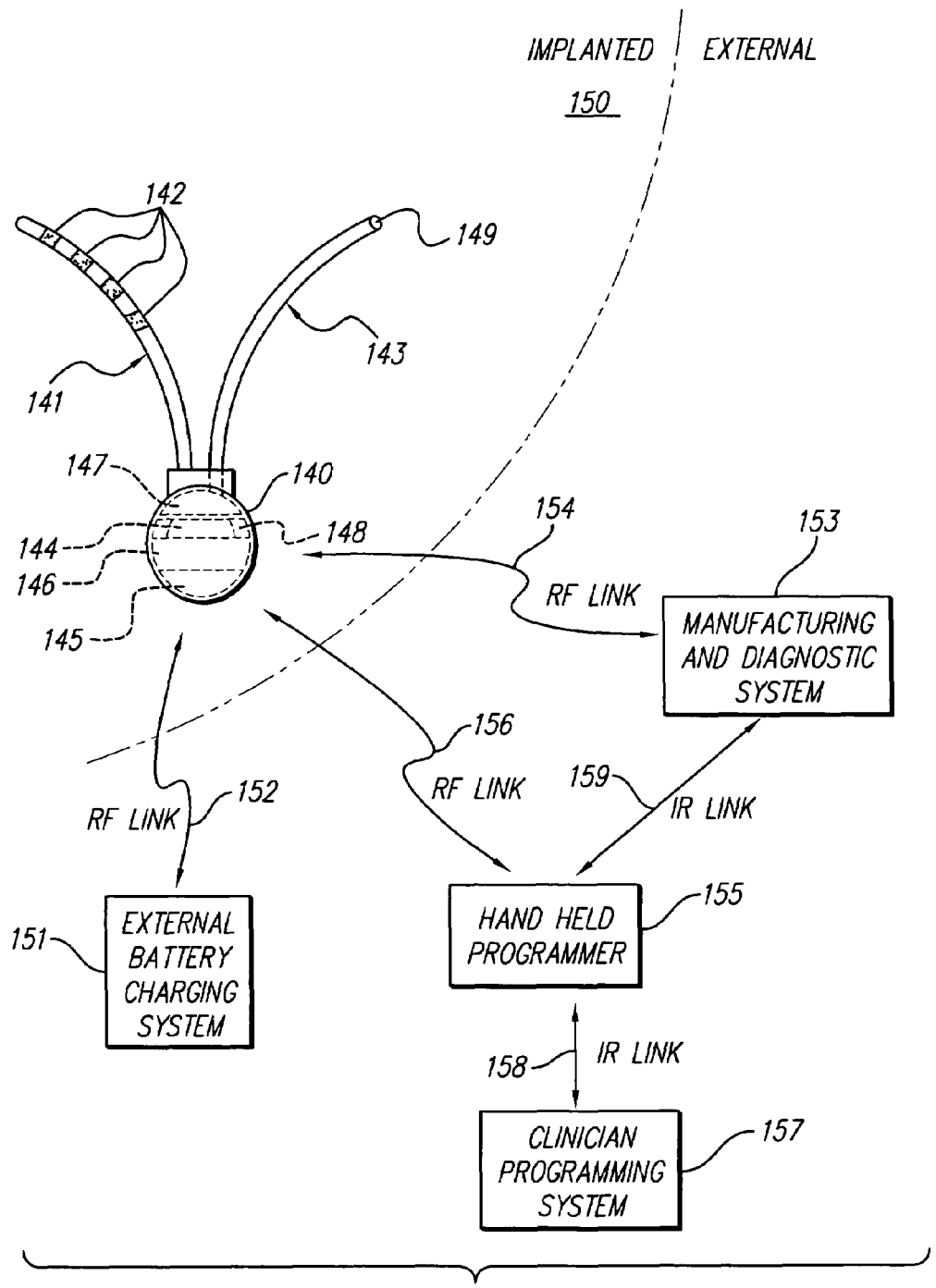
FIG. 2 illustrates an exemplary system control unit (SCU) that may be implanted within a patient and used to apply a stimulus to a target nerve to treat a particular medical condition according to principles described herein.

In some embodiments, the electrical stimulation and/or the drug stimulation may be performed by one or more implantable system control units (SCUs). FIG. 2 illustrates an exemplary SCU (140) that may be implanted within a patient (150) and used to apply a stimulus to a target nerve to treat a particular medical condition, e.g., an electrical stimulation to a target nerve, an infusion of one or more drugs into the target nerve, or both.

FIG. 2 shows a lead (141) having a proximal end that may be coupled to the SCU (140) and that may include a number of electrodes (142) configured to apply a stimulation current to a target nerve. In some embodiments, the lead (141) includes anywhere between two and sixteen electrodes (142). However, the lead (141) may include any number of electrodes (142) as best serves a particular application. The electrodes (142) maybe arranged as an array, for example, having at least two or at least four collinear electrodes. In some embodiments, the electrodes are alternatively inductively coupled to the SCU (140). The lead (141) may be thin (e.g., less than 3 millimeters in diameter) such that the lead (141) may be positioned near a target nerve, for example. Alternatively, as will be described in more detail below, the SCU (140) may be leadless.

As illustrated in FIG. 2, the SCU (140) may include a number of components. A power source (145) is configured to output voltage used to supply the various components within the SCU (140) with power. The power source (145) may be a primary battery, a rechargeable battery, a capacitor, or any other suitable power source. A coil (148) is configured to receive and/or emit a magnetic field (also referred to as a radio frequency (RF) field) that is used to communicate with or receive power from one or more external devices (151, 153, 155). Such communication and/or power transfer may include, but is not limited to, transcutaneously receiving data from the external device, transmitting data to the external device, and/or receiving power used to recharge the power source (145).

For example, an external battery charging system (EBCS) (151) may provide power used to recharge the power source (145) via an RF link (152). External devices including, but not limited to, a hand held programmer (HHP) (155), clinician programming system (CPS) (157), and/or a manufacturing and diagnostic system (MDS) (153) may be configured to activate, deactivate, program, and test the SCU (140) via one or more RF links (154, 156). One or more of these external devices (153, 155, 157) may also be used to control the infusion of one or more drugs into a target nerve to treat a particular medical condition.

Additionally, if multiple external devices are used in the treatment of a patient, there may be some communication among those external devices, as well as with the implanted SCU (140). For example, the CPS (157) may communicate with the HHP (155) via an infrared (IR) link (158) or via any other suitable communication link. Likewise, the MDS (153) may communicate with the HHP (155) via an IR link (159) or via any other suitable communication link.

The HHP (155), MDS (153), CPS (157), and EBCS (151) are merely illustrative of the many different external devices that may be used in connection with the SCU (140). Furthermore, it will be recognized that the functions performed by the HHP (155), MDS (153), CPS (157), and EBCS (151) maybe performed by a single external device. One or more of the external devices (153, 155, 157) maybe embedded in a seat cushion, mattress cover, pillow, garment, belt, strap, pouch, or the like.

The SCU (140) may also include electrical circuitry (144) configured to produce electrical stimulation pulses that are delivered to the target nerve via the electrodes (142). In some embodiments, the SCU (140) may be configured to produce monopolar stimulation. The SCU (140) may alternatively or additionally be configured to produce bipolar stimulation. Monopolar electrical stimulation is achieved, for example, using the stimulator case as an indifferent electrode. Bipolar electrical stimulation is achieved, for example, using one of the electrodes of the electrode array as an indifferent electrode. The electrical circuitry (144) may include one or more processors configured to decode stimulation parameters and generate the stimulation pulses. In some embodiments, the SCU (140) has at least four channels and drives up to sixteen electrodes or more. The electrical circuitry (144) may include additional circuitry such as capacitors, integrated circuits, resistors, coils, and the like configured to perform a variety of functions as best serves a particular application.

The SCU (140) may also include a programmable memory unit (146) for storing one or more sets of data and/or stimulation parameters. The stimulation parameters may include, but are not limited to, electrical stimulation parameters and drug stimulation parameters. The programmable memory (146) allows a patient, clinician, or other user of the SCU (140) to adjust the stimulation parameters such that the electrical stimulation and/or drug stimulation are at levels that are safe and efficacious for a particular medical condition and/or for a particular patient. Electrical stimulation and drug stimulation parameters may be controlled independently. However, in some instances, the electrical stimulation and drug stimulation parameters are coupled, e.g., electrical stimulation may be programmed to occur only during drug stimulation. The programmable memory (146) may be any type of memory unit such as, but not limited to, random access memory (RAM), static RAM (SRAM), a hard drive, or the like.

The electrical stimulation parameters may control various parameters of the stimulation current applied to a target nerve including, but not limited to, the frequency, pulse width, amplitude, burst pattern (e.g., burst on time and burst off time), duty cycle or burst repeat interval, ramp on time and ramp off time of the stimulation current that is applied to the target nerve. The drug stimulation parameters may control various parameters including, but not limited to, the amount of drugs infused into the target nerve, the rate of drug infusion, and the frequency of drug infusion.

Specific electrical stimulation and drug stimulation parameters may have different effects on different types of medical conditions. Thus, in some embodiments, the electrical stimulation and/or drug stimulation parameters may be adjusted by the patient, a clinician, or other user of the SCU (140) as best serves a particular medical condition. The electrical stimulation and/or drug stimulation parameters may also be automatically adjusted by the SCU (140), as will be described below. For example, the amplitude of the stimulus current applied to a target nerve may be adjusted to have a relatively low value to target relatively large diameter fibers of a target nerve. The SCU (140) may also increase excitement of a target nerve by applying a stimulation current having a relatively low frequency to the target nerve (e.g., less than 100 Hz). The SCU (140) may also decrease excitement of a target nerve by applying a relatively high frequency to the target nerve (e.g., greater than 100 Hz). The SCU (140) may also be programmed to apply the stimulation current to a target nerve intermittently or continuously.

As shown in FIG. 2, a pump (147) may also be included within the SCU (140). The pump (147) is configured to store and dispense one or more drugs, for example, through a catheter (143). The catheter (143) is coupled at a proximal end to the SCU (140) and may have an infusion outlet (149) for infusing dosages of the one or more drugs into a predetermined site within a target nerve. In some embodiments, the SCU (140) may include multiple catheters (143) and/or pumps (147) for storing and infusing dosages of the one or more drugs into predetermined sites within the target nerve.

The pump (147) or controlled drug release device described herein may include any of a variety of different drug delivery systems. Controlled drug release devices based upon a mechanical or electromechanical infusion pump may be used. In other examples, the controlled drug release device can include a diffusion-based delivery system, e.g., erosion-based delivery systems (e.g., polymer-impregnated with drug placed within a drug-impermeable reservoir in communication with the drug delivery conduit of a catheter), electrodiffusion systems, and the like. Another example is a convective drug delivery system, e.g., systems based upon electroosmosis, vapor pressure pumps, electrolytic pumps, effervescent pumps, piezoelectric pumps and osmotic pumps.

Exemplary pumps (147) or controlled drug release devices suitable for use as described herein include, but are not necessarily limited to, those disclosed in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,360,019; 4,487,603; 4,627,850; 4,692,147; 4,725,852; 4,865,845; 5,057,318; 5,059,423; 5,112,614; 5,137,727; 5,234,692; 5,234,693; 5,728,396; 6,368,315 and the like. All of these listed patents are incorporated herein by reference in their respective entireties.

Figure 3:
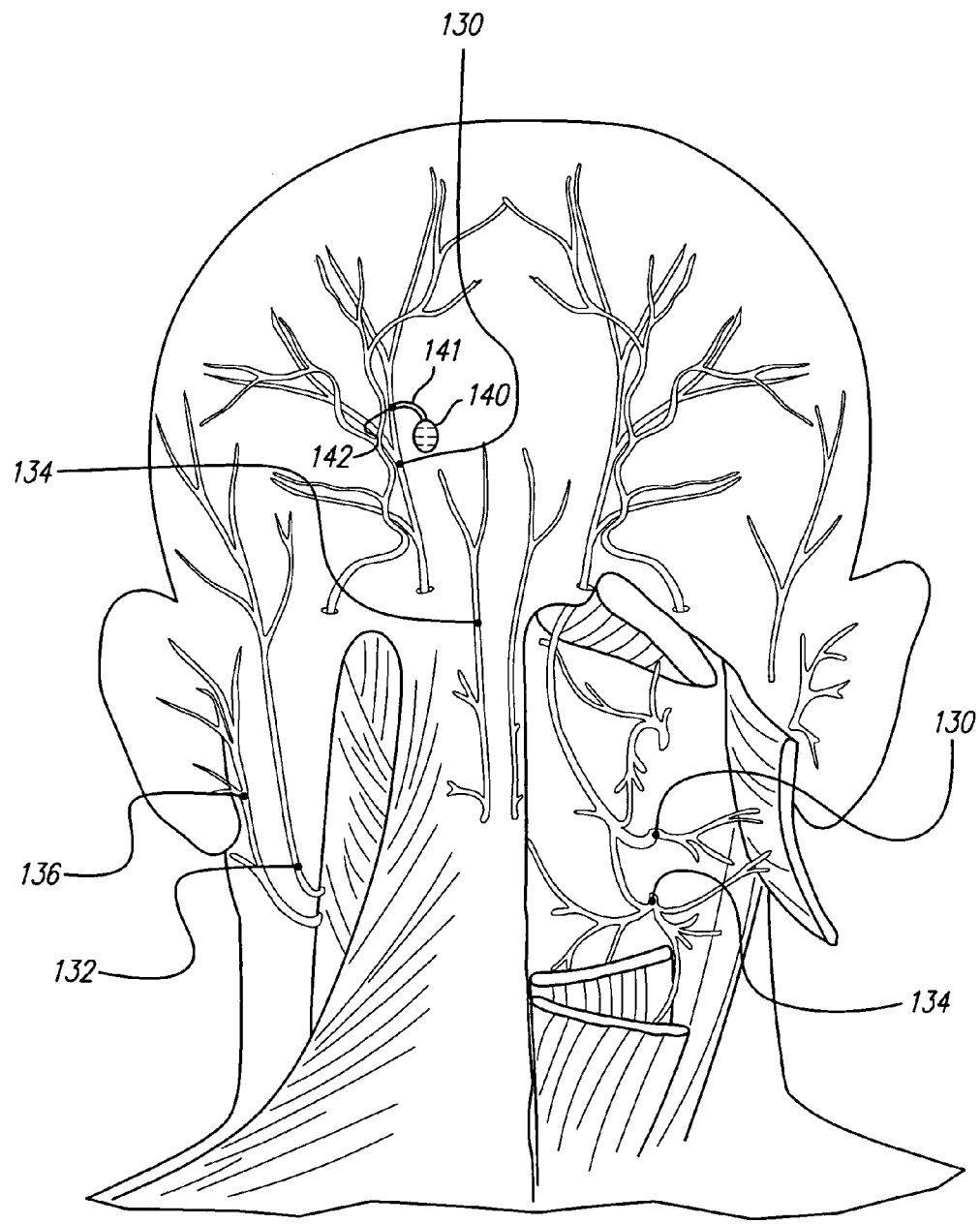
FIG. 3 shows an SCU implanted in the skull relatively near a target nerve according to principles described herein.

The SCU (140) of FIG. 2 may be implanted within the patient (150) using any suitable surgical procedure such as, but not limited to, injection, small incision, open placement, laparoscopy, or endoscopy. In some instances, the SCU (140) may be implanted at a site that is relatively close to a target nerve with the lead (141) and/or the catheter (143) being routed to the target nerve. For example, FIG. 3 shows an SCU (140) implanted in the skull relatively near a target nerve. The target nerve in the example of FIG. 3 is the greater occipital nerve (130) for illustrative purposes only. As shown in FIG. 3, the SCU (140) is coupled to a short lead (141) having a distal end coupled to the target greater occipital nerve (130). The lead (141) may include one or more electrodes (142) that are coupled directly to the target nerve (130). As will be described in more detail below, the SCU (140) itself may alternatively be coupled directly to the target nerve (130).

The SCU (140) of FIG. 2 is illustrative of many types of SCUs that may be used to apply electrical stimulation to a target nerve and/or infuse one or more drugs into the target nerve to treat a particular medical condition. In general, the SCU (140) may be any relatively small implantable device (e.g., substantially equal to or less than three cubic centimeters (cc)) configured to apply electrical and/or drug stimulation to a target nerve. For example, the SCU (140) may include an implantable pulse generator (IPG) coupled to one or more leads (141) having a number of electrodes (142). Exemplary IPGs suitable for use as described herein include, but are not necessarily limited to, those disclosed in U.S. Pat. Nos. 6,381,496; 6,553,263; and 6,760,626. In the case of drug stimulation only, the SCU (140) comprises a pump. Alternatively, the SCU (140) may be an implantable microstimulator, such as a BION® microstimulator (Advanced Bionics® Corporation, Valencia, Calif.). The following listed patents describe various details associated with the manufacture, operation, and use of BION implantable microstimulators, and are all incorporated herein by reference in their respective entireties:

| Application/Patent/ Publication No. | Filing/Publication Date | Title |
| --- | --- | --- |
| U.S. Pat. No. 5,193,539 | Issued Mar. 16, 1993 | Implantable Microstimulator |
| U.S. Pat. No. 5,193,540 | Issued Mar. 16, 1993 | Structure and Method of Manufacture of an Implantable Microstimulator |
| U.S. Pat. No. 5,312,439 | Issued May 17, 1994 | Implantable Device Having an Electrolytic Storage Electrode |
| U.S. Pat. No. 6,185,452 | Issued Feb. 6, 2001 | Battery-Powered Patient Implantable Device |
| U.S. Pat. No. 6,164,284 | Issued Dec. 26, 2000 | System of Implantable Devices For Monitoring and/or Affecting Body Parameters |
| U.S. Pat. No. 6,208,894 | Issued Mar. 27, 2001 | System of Implantable Devices For Monitoring and/or Affecting Body Parameters |
| U.S. Pat. No. 6,051,017 | Issued Apr. 18, 2000 | Implantable Microstimulator and Systems Employing Same |

Figure 4:
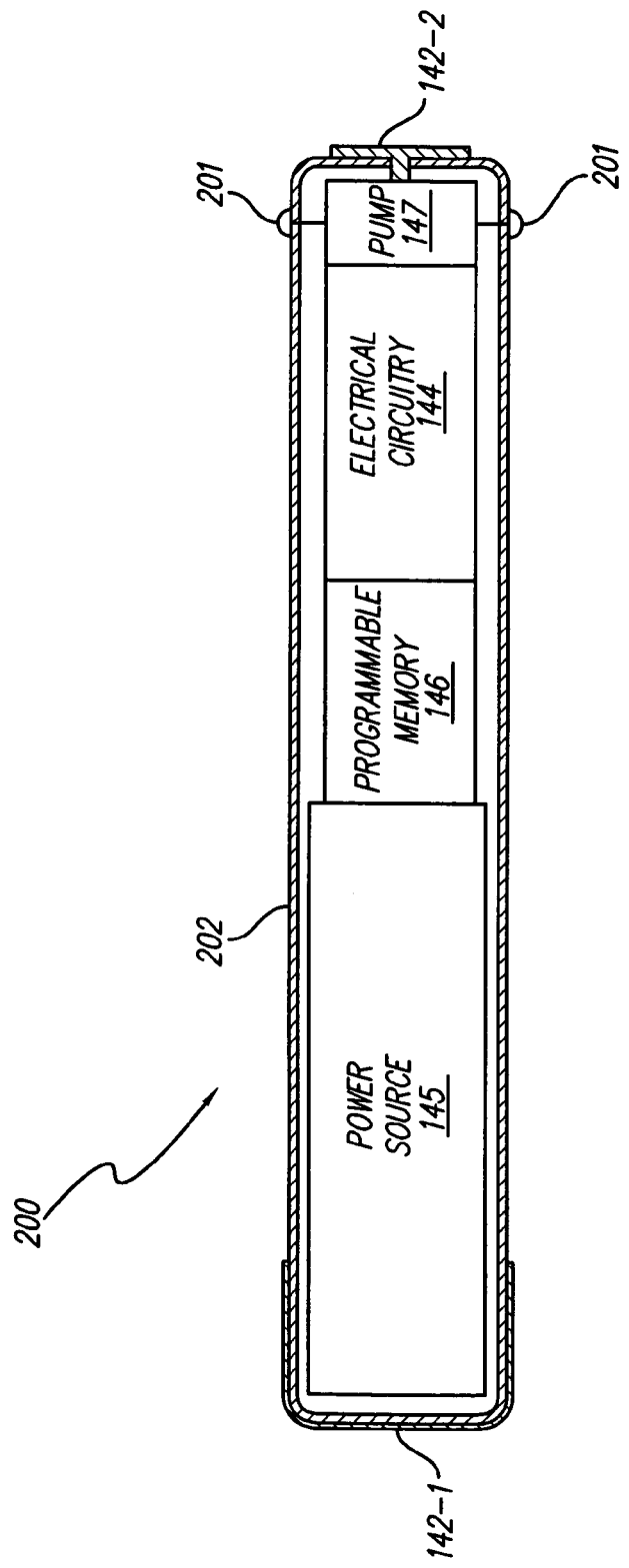
FIG. 4 illustrates an exemplary BION microstimulator that may be used as the SCU according to principles described herein.

FIG. 4 illustrates an exemplary BION microstimulator (200) that may be used as the SCU (140; FIG. 2) described herein. Other configurations of the microstimulator (200) are possible, as shown in the above-referenced patents and as described further below.

As shown in FIG. 4, the microstimulator (200) may include the power source (145), the programmable memory (146), the electrical circuitry (144), and the pump (147) described in connection with FIG. 2. These components are housed within a capsule (202). The capsule (202) may be a thin, elongated cylinder or any other shape as best serves a particular application. The shape of the capsule (202) may be determined by the structure of the desired target nerve, the surrounding area, and the method of implementation. In some embodiments, the capsule (202) is substantially equal to or less than three cubic centimeters.

In some embodiments, the microstimulator (200) may include two or more leadless electrodes (142). Either or both of the electrodes (142) may alternatively be located at the ends of short, flexible leads as described in U.S. patent application Ser. No. 09/624,130, filed Jul. 24, 2000, which is incorporated herein by reference in its entirety. The use of such leads permits, among other things, electrical stimulation to be directed more locally to targeted tissue(s) a short distance from the surgical fixation of the bulk of the microstimulator (200), while allowing most elements of the microstimulator (200) to be located in a more surgically convenient site. This minimizes the distance traversed and the surgical planes crossed by the microstimulator (200) and any lead(s).

The external surfaces of the microstimulator (200) may advantageously be composed of biocompatible materials. For example, the capsule (202) may be made of glass, ceramic, metal, or any other material that provides a hermetic package that will exclude water vapor but permit passage of electromagnetic fields used to transmit data and/or power. The electrodes (142) may be made of a noble or refractory metal or compound, such as platinum, iridium, tantalum, titanium, titanium nitride, niobium or alloys of any of these, in order to avoid corrosion or electrolysis which could damage the surrounding tissues and the device.

Figure 5:
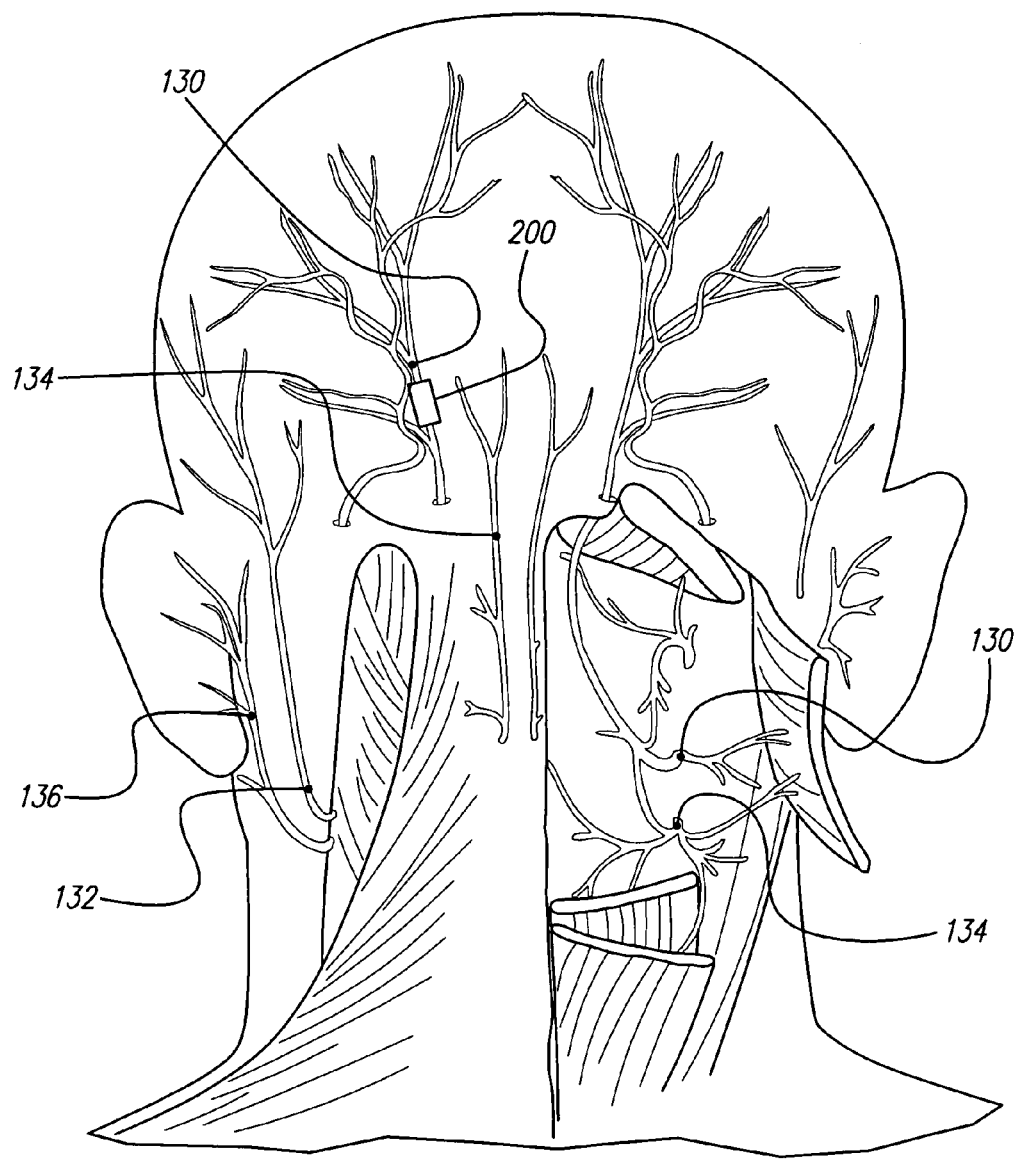
FIG. 5 shows the microstimulator coupled directly to a target nerve according to principles described herein.

The microstimulator (200) may be implanted within a patient with a surgical tool such as a hypodermic needle, bore needle, or any other tool specially designed for the purpose. Alternatively, the microstimulator (200) may be implanted using endoscopic or laparoscopic techniques. As previously mentioned and as shown in FIG. 5, the microstimulator (200) may be coupled directly to a target nerve. FIG. 5 shows the microstimulator (200) coupled directly to the greater occipital nerve (130).

Returning to FIG. 4, the microstimulator (200) may include one or more infusion outlets (201). The infusion outlets (201) facilitate the infusion of one or more drugs into a treatment site to treat a particular medical condition. The infusion outlets (201) may dispense one or drugs directly to the treatment site. Alternatively, as will be described in more detail below, catheters may be coupled to the infusion outlets (201) to deliver the drug therapy to a treatment site some distance from the body of the microstimulator (200). The stimulator (200) of FIG. 4 also includes electrodes (142-1 and 142-2) at either end of the capsule (202). One of the electrodes (142) may be designated as a stimulating electrode to be placed close to the treatment site and one of the electrodes (142) may be designated as an indifferent electrode used to complete a stimulation circuit.

Figure 6:
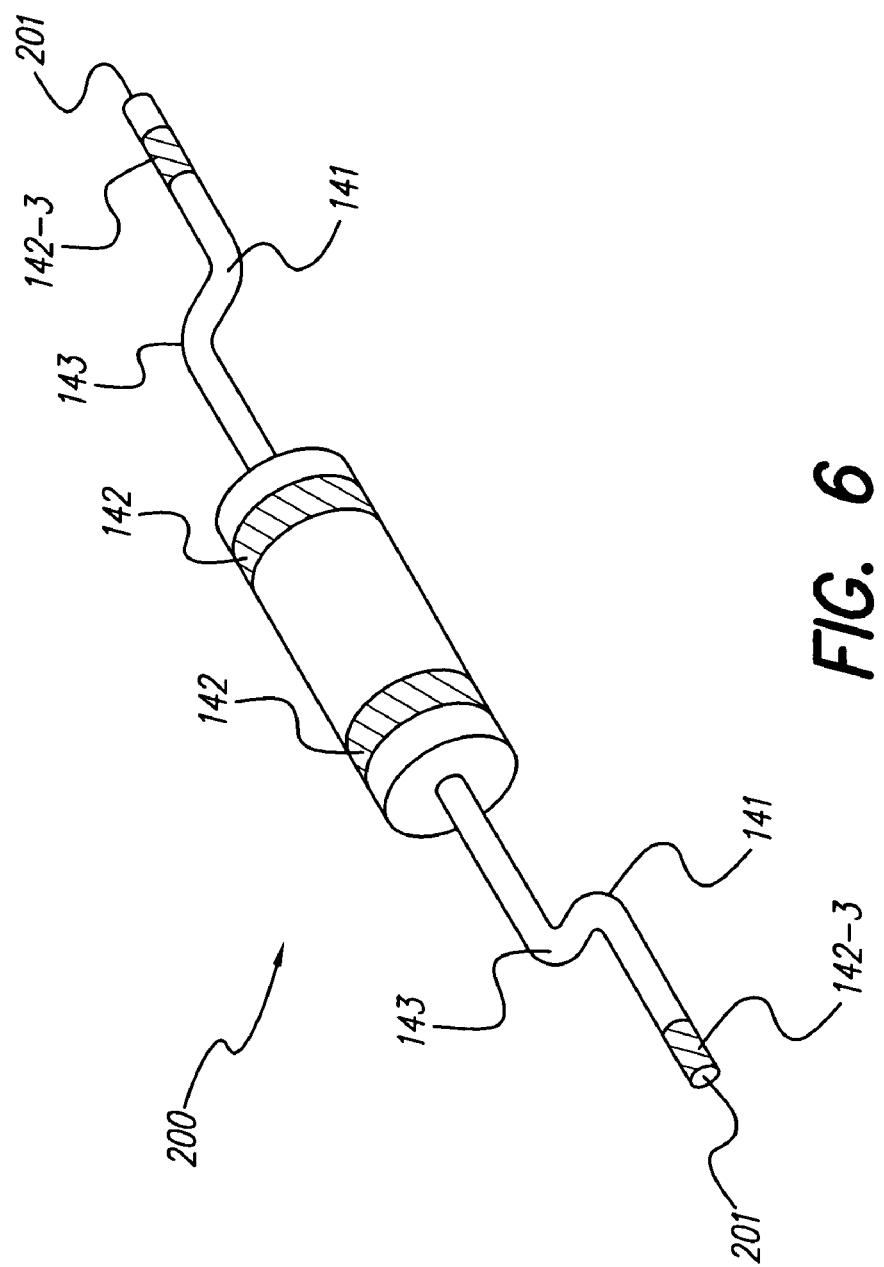
FIG. 6 shows one or more catheters coupled to the microstimulator according to principles described herein.

FIG. 6 shows an example of a microstimulator (200) with one or more catheters (143) coupled to the infusion outlets on the body of the microstimulator (200). With the catheters (143) in place, the infusion outlets (201) that actually deliver the drug therapy to target tissue are located at the end of each catheter (143). Thus, in the example of FIG. 6, a drug therapy is expelled by the pump (147, FIG. 4) from an infusion outlet (201, FIG. 4) in the casing (202, FIG. 4) of the microstimulator (200), through the catheter (143), out an infusion outlet (201) at the end of the catheter (143) to the target site within the patient. As shown in FIG. 6, the catheters (143) may also serve as leads (141) having one or more electrodes (142-3) disposed thereon. Thus, the catheters (143) and leads (141) of FIG. 6 permit infused drugs and/or electrical stimulation to be directed to a treatment site while allowing most elements of the microstimulator (200) to be located in a more surgically convenient site. The example of FIG. 6 may also include leadless electrodes (142) disposed on the housing of the microstimulator (200), in the same manner described above.

Returning to FIG. 2, the SCU (140) may be configured to operate independently. Alternatively, the SCU (140) may be configured to operate in a coordinated manner with one or more additional SCUs (140), other implanted devices, or other devices external to the patient's body. For instance, a first SCU (140) may control or operate under the control of a second SCU (140), other implanted device, or other device external to the patient's body. The SCU (140) may be configured to communicate with other implanted SCUs (140), other implanted devices, or other devices external to the patient's body via an RF link, an untrasonic link, an optical link, or any other type of communication link. For example, the SCU (140) may be configured to communicate with an external remote control that is capable of sending commands and/or data to the SCU (140) and that is configured to receive commands and/or data from the SCU (140).

In order to determine the amount and/or type(s) of stimulating drug(s) and/or the strength and/or duration of electrical stimulation required to most effectively treat a particular medical condition, various indicators of the medical condition and/or a patient's response to treatment may be sensed or measured. These indicators include, but are not limited to, muscle or limb activity (e.g., electromyography (EMG)), electrical activity of the brain (e.g., EEG), neurotransmitter levels, hormone levels, and/or medication levels. In some embodiments, the SCU (140) may be configured to change the stimulation parameters in a closed loop manner in response to these measurements. The SCU (140) may be configured to perform the measurements. Alternatively, other sensing devices may be configured to perform the measurements and transmit the measured values to the SCU (140).

Thus, it is seen that one or more external appliances may be provided to interact with the SCU (140), and may be used to accomplish at least one or more of the following functions:

Function 1: If necessary, transmit electrical power to the SCU (140) in order to power the SCU (140) and/or recharge the power source (145).

Function 2: Transmit data to the SCU (140) in order to change the stimulation parameters used by the SCU (140).

Function 3: Receive data indicating the state of the SCU (140) (e.g., battery level, drug level, stimulation parameters, etc.).

Additional functions may include adjusting the stimulation parameters based on information sensed by the SCU (140) or by other sensing devices.

By way of example, an exemplary method of treating a particular medical condition within a patient may be carried out according to the following sequence of procedures. The steps listed below may be modified, reordered, and/or added to as best serves a particular application.

1. An SCU (140) is implanted so that its electrodes (142) and/or infusion outlet (149) are coupled to or located near a target nerve. If the SCU (140) is a microstimulator, such as the BION microstimulator (200; FIG. 4), the microstimulator itself may be coupled to the target nerve.

2. The SCU (140) is programmed to apply at least one stimulus to the target nerve. The stimulus may include electrical stimulation and/or drug stimulation.

3. When the patient desires to invoke electrical and/or drug stimulation, the patient sends a command to the SCU (140) (e.g., via a remote control) such that the SCU (140) delivers the prescribed electrical and/or drug stimulation. The SCU (140) may be alternatively or additionally configured to automatically apply the electrical and/or drug stimulation in response to sensed indicators of the particular medical condition.

4. To cease electrical and/or drug stimulation, the patient may turn off the SCU (140) (e.g., via a remote control).

5. Periodically, the power source (145) of the SCU (140) is recharged, if necessary, in accordance with Function 1 described above.

For the treatment of any of the various types of medical conditions, it may be desirable to modify or adjust the algorithmic functions performed by the implanted and/or external components, as well as the surgical approaches. For example, in some situations, it may be desirable to employ more than one SCU (140), each of which could be separately controlled by means of a digital address. Multiple channels and/or multiple patterns of electrical and/or drug stimulation may thereby be used to deal with multiple medical conditions.

Figure 7:
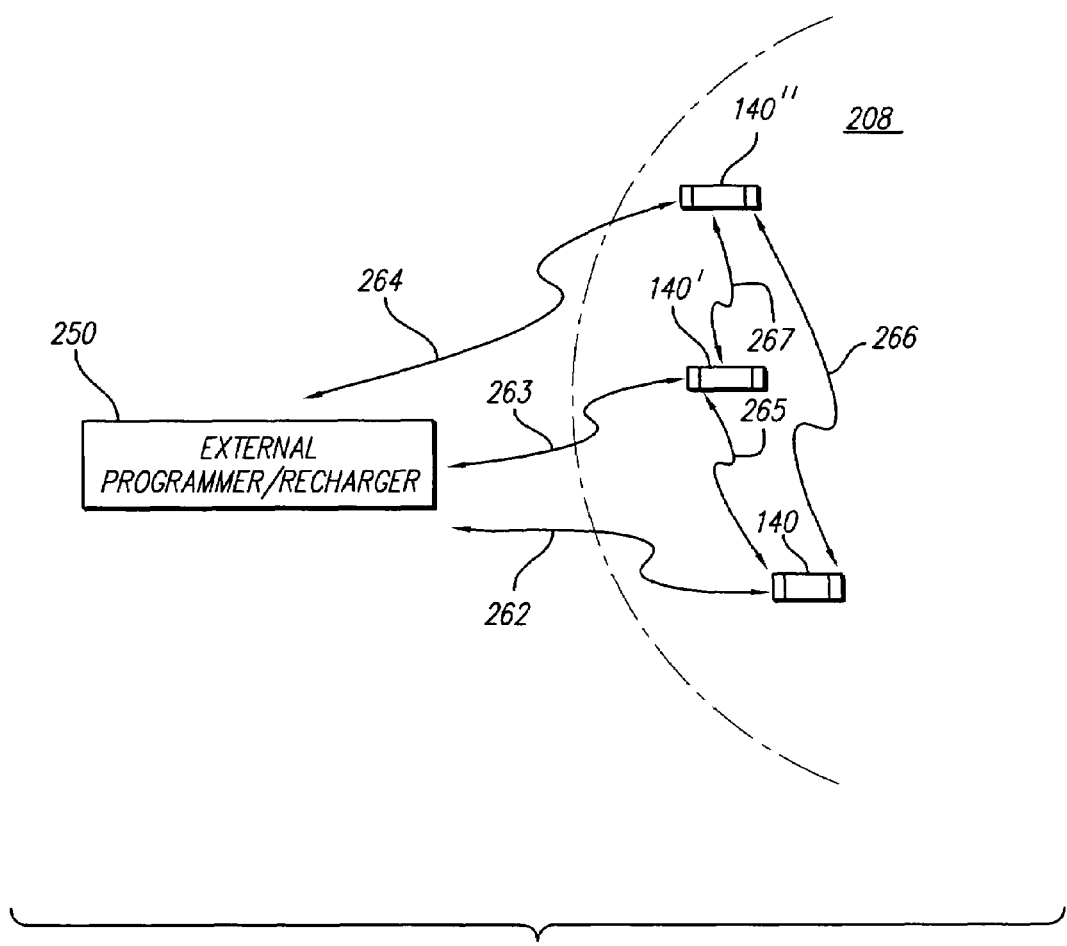
FIG. 7 depicts a number of SCUs configured to communicate with each other and/or with one or more external devices according to principles described herein.

For instance, as shown in the example of FIG. 7, a first SCU (140) implanted beneath the skin of the patient (208) provides a stimulus to a first location; a second SCU (140') provides a stimulus to a second location; and a third SCU (140") provides a stimulus to a third location. As mentioned earlier, the implanted devices may operate independently or may operate in a coordinated manner with other implanted devices or other devices external to the patient's body. That is, an external controller (250) may be configured to control the operation of each of the implanted devices (140, 140', and 140"). In some embodiments, an implanted device, e.g. SCU (140), may control or operate under the control of another implanted device(s), e.g. SCU (140') and/or SCU (140"). Control lines (262-267) have been drawn in FIG. 7 to illustrate that the external controller (250) may communicate or provide power to any of the implanted devices (140, 140', and 140") and that each of the various implanted devices (140, 140', and 140") may communicate with and, in some instances, control any of the other implanted devices.

As a further example of multiple SCUs (140) operating in a coordinated manner, the first and second SCUs (140, 140') of FIG. 7 may be configured to sense various indicators of a particular medical condition and transmit the measured information to the third SCU (140"). The third SCU (140") may then use the measured information to adjust its stimulation parameters and apply electrical and/or drug stimulation to a target nerve accordingly.

Alternatively, the external device (250) or other external devices communicating with the external device may be configured to sense various indicators of a patient's condition. The sensed indicators can then be transmitted to the external device (250) or to one or more of the implanted SCUs which may adjust stimulation parameters accordingly. In other examples, the external controller (250) may determine whether any change to stimulation parameters is needed based on the sensed indicators. The external device (250) may then signal a command to one or more of the SCUs to adjust stimulation parameters accordingly.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method of treating a medical condition of a patient, said method comprising:
    applying at least one stimulus to a target nerve within a patient with an implanted system control unit in accordance with one or more stimulation parameters configured to treat said medical condition;
    wherein said target nerve comprises a nerve originating in an upper cervical spine area of said patient and wherein said medical condition comprises at least one or more of an autoimmune disease, hyperthyroidism, and hypothyroidism.

2. The method of claim 1, wherein said target nerve comprises at least one or more of a greater occipital nerve, a lesser occipital nerve, a third occipital nerve, a greater auricular nerve, a transverse cervical nerve, and a supraclavicular nerve.

3. The method of claim 1 further comprising coupling said system control unit to said target nerve.

4. The method of claim 1, wherein said system control unit is coupled to one or more electrodes, and wherein said stimulus comprises a stimulation current delivered via said electrodes.

5. The method of claim 1, wherein said stimulus comprises one or more drugs delivered to said target nerve.

6. The method of claim 1, wherein said stimulus comprises a stimulation current delivered to said target nerve and a stimulation via one or more drugs delivered to said target nerve.

7. The method of claim 1, further comprising sensing at least one indicator related to said medical condition and using said at least one sensed indicator to adjust one or more of said stimulation parameters.

8. The method of claim 1, wherein said system control unit comprises a microstimulator.

9. The method of claim 1, wherein said system control unit has dimensions substantially equal to or less than three cubic centimeters.

10. A system for treating a medical condition of a patient, said system comprising:
a system control unit configured to be implanted at least partially within a patient and to generate at least one stimulus in accordance with one or more stimulation parameters configured to treat said medical condition;
a programmable memory unit in communication with said system control unit and programmed to store said one or more stimulation parameters to at least partially define said at least one stimulus such that said at least one stimulus is configured to treat said medical disorder when applied to a target nerve originating in an upper cervical spine area of said patient; and
means, operably connected to said system control unit, for applying said stimulus to said target nerve;
wherein said medical condition comprises at least one or more of an autoimmune disease, hyperthyroidism, and hypothyroidism.

11. The system of claim 10 wherein said target nerve comprises at least one or more of a greater occipital nerve, a lesser occipital nerve, a third occipital nerve, a greater auricular nerve, a transverse cervical nerve, and a supraclavicular nerve.

12. The system of claim 10, wherein said system control unit is coupled directly to said target nerve.

13. The system of claim 10 wherein said system control unit is coupled to one or more electrodes, and wherein said stimulus comprises a stimulation current delivered via said electrodes.

14. The system of claim 10, wherein said stimulus comprises stimulation via one or more drugs delivered to said target nerve.

15. The system of claim 10, wherein said stimulus comprises a stimulation current delivered to said target nerve and one or more drugs delivered to said target nerve.

16. The system of claim 10, further comprising:
a sensor device for sensing at least one indicator related to said medical condition;
wherein said system control unit uses said at least one sensed indicator to adjust one or more of said stimulation parameters.

17. The system of claim 10, wherein said system control unit comprises a microstimulator.

18. The system of claim 10, wherein said system control unit has dimensions substantially equal to or less than three cubic centimeters.

19. A method of treating a medical disorder, said method comprising:
implanting a system control unit within a patient;
programming said system control unit with one or more stimulation parameters configured to treat said medical disorder; and
applying an electrical stimulation current with said system control unit to a nerve originating in an upper cervical spine area of said patient in accordance with said one or more stimulation parameters;
wherein said medical condition comprises at least one or more of an autoimmune disease, hyperthyroidism, and hypothyroidism.

20. The method of claim 19, wherein said target nerve comprises at least one or more of a greater occipital nerve, a lesser occipital nerve, a third occipital nerve, a greater auricular nerve, a transverse cervical nerve, and a supraclavicular nerve.

* * * * *